US008921760B2

United States Patent
Qi et al.

(10) Patent No.: US 8,921,760 B2
(45) Date of Patent: Dec. 30, 2014

(54) DETECTING APPARATUS FOR DETERMINING LIQUID CRYSTAL GLASSES DISPLACEMENT IN A CARTRIDGE

(71) Applicant: Shenzhen China Star Optoelectronics Technology Co., Ltd., Shenzhen (CN)

(72) Inventors: Minghu Qi, Shenzhen (CN); Chunhao Wu, Shenzhen (CN); Kunhsien Lin, Shenzhen (CN); Yongqiang Wang, Shenzhen (CN); Zhenhua Guo, Shenzhen (CN); Weibing Yang, Shenzhen (CN); Zenghong Chen, Shenzhen (CN); Yunshao Jiang, Shenzhen (CN); Zhiyou Shu, Shenzhen (CN)

(73) Assignee: Shenzhen China Star Optoelectronics Technology Co., Ltd., Shenzhen, Guangdong (CN)

( * ) Notice: Subject to any disclaimer, the term of this patent is extended or adjusted under 35 U.S.C. 154(b) by 265 days.

(21) Appl. No.: 13/806,902

(22) PCT Filed: Nov. 20, 2012

(86) PCT No.: PCT/CN2012/084917
§ 371 (c)(1),
(2), (4) Date: Dec. 26, 2012

(87) PCT Pub. No.: WO2014/075325
PCT Pub. Date: May 22, 2014

(65) Prior Publication Data
US 2014/0131558 A1    May 15, 2014

(30) Foreign Application Priority Data

Nov. 13, 2012  (CN) .......................... 2012 1 0452876

(51) Int. Cl.
*H01J 40/14*   (2006.01)
*G01V 8/14*    (2006.01)

(52) U.S. Cl.
CPC ........................................ *G01V 8/14* (2013.01)
USPC .......................................... 250/221; 250/577

(58) Field of Classification Search
USPC ................... 250/221, 577, 573, 576, 223 B; 209/526, 577; 356/341–344, 427; 347/7, 14
See application file for complete search history.

(56) References Cited

U.S. PATENT DOCUMENTS 5,523,560 A * 6/1996 Manique et al. .......... 250/223 B

* cited by examiner

Primary Examiner — Que T Le
(74) Attorney, Agent, or Firm — Andrew C. Cheng

(57) ABSTRACT

A detecting apparatus for determining whether liquid crystal glasses are displaced in a cartridge is disclosed. The detecting apparatus includes: a signal sensing device for sending sensing signals to an internal of the cartridge and for receiving the reflected signals from the internal of the cartridge; a reflector installed in the internal of the cartridge for receiving the sensing signals from the signal sensing device and for reflecting the sensing signals back to the signal sensing device; and wherein a determination of whether the liquid crystal glass is displaced in the cartridge is made by determining whether the reflected signals from the reflector are received after the sensing signals are sent. Upon determining whether liquid crystal glasses are displaced in the cartridge, impurities are prevented from getting into the cartridge and thus the cleanliness is enhanced and the labor power is reduced.

18 Claims, 3 Drawing Sheets

DETECTING APPARATUS FOR DETERMINING LIQUID CRYSTAL GLASSES DISPLACEMENT IN A CARTRIDGE

This application claims priority to China Patent Application No. 201210452876.0 filed on Nov. 13, 2012 entitled, DETECTING APPARATUS FOR DETERMINING EMPTY CARTRIDGE, all of the disclosures of which are incorporated herein by reference in their entirety.

BACKGROUND OF THE INVENTION

1. Field of the Invention

Embodiments of the present disclosure relate to liquid crystal display technology, and more particularly to a detecting apparatus for determining an empty cartridge.

2. Discussion of the Related Art

With the technology development, liquid crystal displays are the most popular displays. The liquid crystal panel is a key component for the liquid crystal display. In the manufacturing process, the liquid crystal glasses are stored in cartridges of stacking machines. Sensing signals devices are usually adopted to detect whether the liquid crystal glasses are in the cartridges. A reflective signal sensing device is adopted for a more precise detection.

The typical reflective signal sensing devices have the following problems. First, as a through hole is needed on a top plate of the cartridge, dust or particles may get into the cartridge via the through hole so that the liquid crystal glasses are polluted. FIG. 5 shows a typical cartridge with one through hole on the top plate. As shown in FIG. 5, the through hole 91 is on the top plate 92 of the cartridge. The paths of the sensing signals are shown in FIG. 5 with dashed lines b. Second. In order to keep the liquid crystal glasses from being polluted, labor cost are needed to clean the cartridge frequently.

SUMMARY

The object of the claimed invention is to provide a detecting apparatus for determining an empty cartridge. In the process of detecting whether liquid crystal glasses are displaced in the cartridge, impurities are prevented from getting into the cartridge and thus the cleanliness is enhanced and the labor power is reduced.

In one aspect, a detecting apparatus for determining whether liquid crystal glasses are displaced in a cartridge includes: an electro-optical sensing device for sending sensing signals to an internal of the cartridge and for receiving the reflected signals from the internal of the cartridge; a reflective plate installed in the internal of the cartridge for receiving the sensing signals from the electro-optical sensing device and for reflecting the sensing signals back to the electro-optical sensing device; and wherein a determination of whether the liquid crystal glass is displaced in the cartridge is made by determining whether the reflected signals from the reflective plate are received after the sensing signals are sent.

Wherein the cartridge comprises a top plate, and the reflective plate is installed on an internal surface of the top plate.

Wherein the electro-optical sensing device is installed in an external side of a bottom of the cartridge.

Wherein the sensing signals are sent from the bottom of the cartridge toward the top plate.

Wherein the reflective plate is installed on an internal surface of the top plate capable of receiving the sensing signals.

In another aspect, a detecting apparatus for determining whether liquid crystal glasses are displaced in a cartridge includes: an electro-optical sensing device for sending optical signals to an internal of the cartridge and for receiving the reflected signals from the internal of the cartridge; a reflective plate installed in the internal of the cartridge for receiving the optical signals from the electro-optical sensing device and for reflecting the optical signals back to the electro-optical sensing device; and wherein a determination of whether the liquid crystal glass is displaced in the cartridge is made by determining whether the reflected signals from the reflective plate are received after the optical signals are sent.

Wherein the cartridge comprises a top plate, and the reflective plate is installed on an internal surface of the top plate.

Wherein the electro-optical sensing device is installed in an external side of a bottom of the cartridge.

Wherein the optical signals are sent from the bottom of the cartridge toward the top plate.

Wherein the reflective plate is installed on an internal surface of the top plate capable of receiving the optical signals.

In another aspect, a detecting apparatus for determining whether liquid crystal glasses are displaced in a cartridge includes: a signal sensing device for sending sensing signals to an internal of the cartridge and for receiving the reflected signals from the internal of the cartridge; a reflector installed in the internal of the cartridge for receiving the sensing signals from the signal sensing device and for reflecting the sensing signals back to the signal sensing device; and wherein a determination of whether the liquid crystal glass is displaced in the cartridge is made by determining whether the reflected signals from the reflector are received after the sensing signals are sent.

Wherein the cartridge comprises a top plate, and the reflector is installed on an internal surface of the top plate.

Wherein the signal sensing device is installed in an external side of a bottom of the cartridge.

Wherein the sensing signals are sent from the bottom of the cartridge toward the top plate.

Wherein the reflector is installed on an internal surface of the top plate capable of receiving the sensing signals.

Wherein the reflector is a reflective plate.

Wherein the signal sensing device is an electro-optical sensing device.

Wherein the sensing signals are optical signals.

DETAILED DESCRIPTION OF THE EMBODIMENTS

Embodiments of the invention will now be described more fully hereinafter with reference to the accompanying drawings, in which embodiments of the invention are shown.

FIGS. 1-4 show a detecting apparatus for determining an empty cartridge in accordance with one embodiment.

The detecting apparatus includes a cartridge 1, a plurality of supports 11 installed in the cartridge 1, a plurality of liquid crystal glasses 2 displaced on the supports 11, and a detecting device for detecting whether the cartridge is empty.

Figure 1:
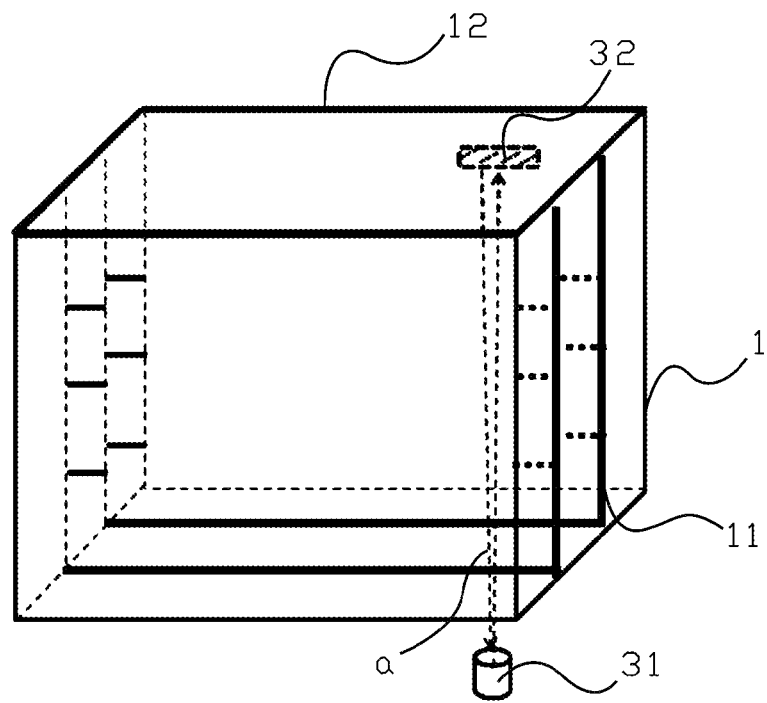
FIG. 1 is a perspective view of the detecting apparatus for determining an empty cartridge in accordance with one embodiment.
Figure 3:
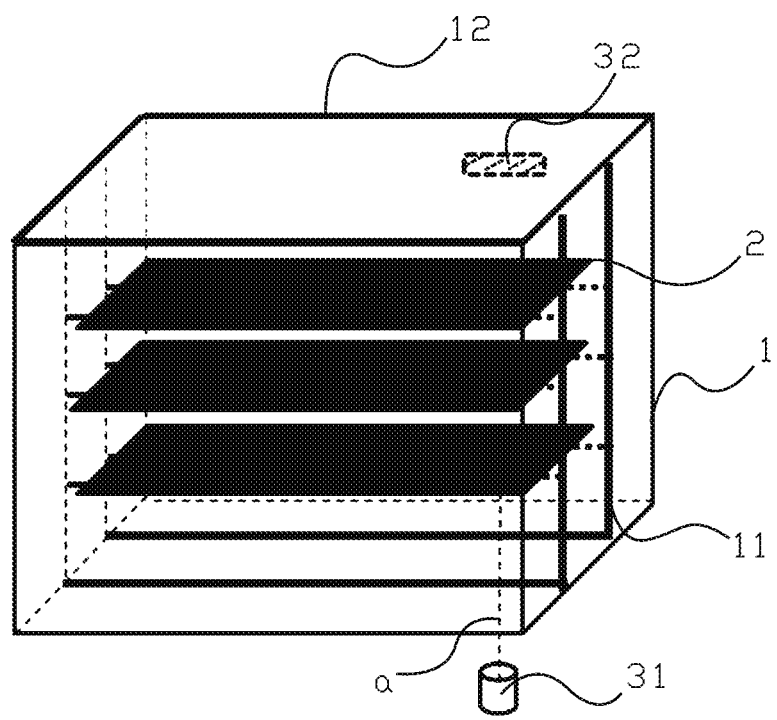
FIG. 3 is a perspective view of the detecting apparatus and the cartridge with liquid crystal glasses stored therein.

FIG. 1 is a perspective view of the detecting apparatus for determining an empty cartridge in accordance with one embodiment. The cartridge 1 is a cubic structure formed by a plurality of frame strips. As shown in FIG. 3, the space defined by the frame strips is for displacing the liquid crystal glasses 2.

The liquid crystal glasses 2 are displaced on the supports 11 of the cartridge 1. The supports 11 are arranged in multiple layers in a vertical direction. In the embodiment, the supports 11 are arranged in three layers, and the liquid crystal glasses 2 are displaced in each of the layers.

The cartridge 1 includes a top plate 12 for preventing the dust and the impurities from getting into the cartridge 1.

The detecting device includes a signal sensing device 31 for sending sensing signals to an internal of the cartridge 1 and for receiving the reflected signals from the internal of the cartridge 1.

A reflector 32 installed in the internal of the cartridge 1 for receiving the sensing signals from the signal sensing device 31 and for sending the sensing signals back to the signal sensing device 31.

After the sensing signals are sent by the signal sensing device 31, a determination of whether the liquid crystal glass 2 is displaced in the cartridge 1 is made by determining whether the reflected signals from the reflector 32 are received after the sensing signals are sent The signal sensing device 31 is an electro-optical sensor capable of sending optical signals. The reflected optical signals are received by the reflector 32 when there is no obstacle between the signal sensing device 31 and the reflector 32. The paths of the optical signals from the signal sensing device 31 are shown by dashed lines. As the optical signals are more precise than sensing signals and the response time of the optical signals are faster, the determination may be made in an efficient way.

The electro-optical sensing device 31 is installed in an external side of a bottom of the cartridge 1. The optical signals from the signal sensing device 31 may be sent from the bottom of the cartridge 1 toward the top plate 12.

The reflector 32 is a reflective plate. As the dimension of the reflective plate is small and thus does not occupy the space for the liquid crystal glass 2. The reflector 32 is installed on an internal surface of the top plate 12 such that the reflector 32 is capable of receiving the optical signals sent from the bottom of the cartridge 1 toward the top plate 12.

Furthermore, the location of the reflective plate 32 aligns with the location of the electro-optical sensing device 31 such that the reflective plate 32 is capable of reflecting the optical signals.

During the detecting process, as the reflective plate 32 is installed on the internal surface of the top plate 12, the optical signals are directly sent to the reflective plate 32. The optical signals are reflected without passing through the top plate 12. In this way, as there is no through hole on the top plate 12, particles are prevented from getting into the cartridge 1 so that the liquid crystal glass 2 are not polluted.

Figure 2:
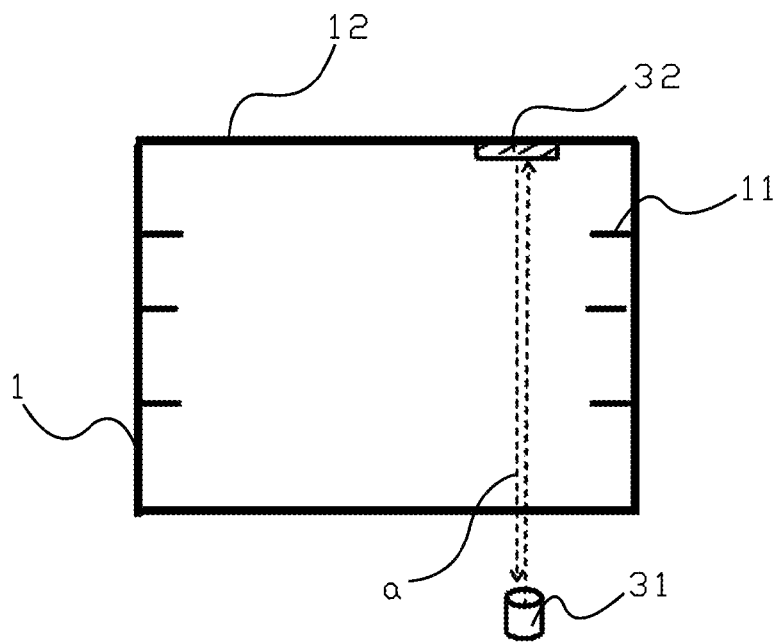
FIG. 2 is a side view of the detecting apparatus for determining the empty cartridge in accordance with one embodiment.

The detecting process is described with reference to FIG. 2.

The electro-optical sensing device 31 arranged in the external side of the bottom of the cartridge 1 sends the optical signals from the bottom of the cartridge 1 toward the top plate 12. As the cartridge 1 is empty, the reflective plate 32 receives the optical signals in time and reflects the optical signals back. In this way, the detecting device determines the cartridge 1 is empty.

Figure 4:
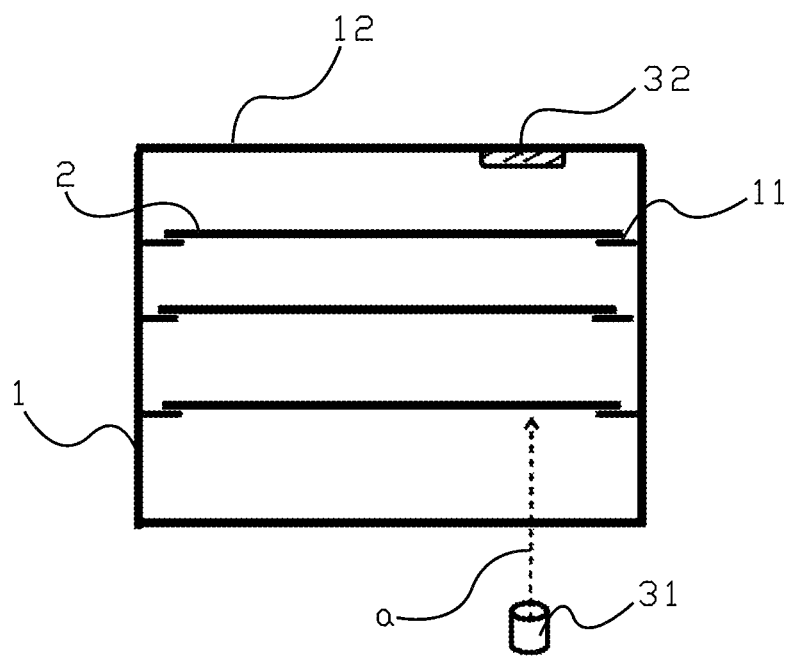
FIG. 4 is a side view of the detecting apparatus and the cartridge with liquid crystal glasses stored therein.
Figure 5:
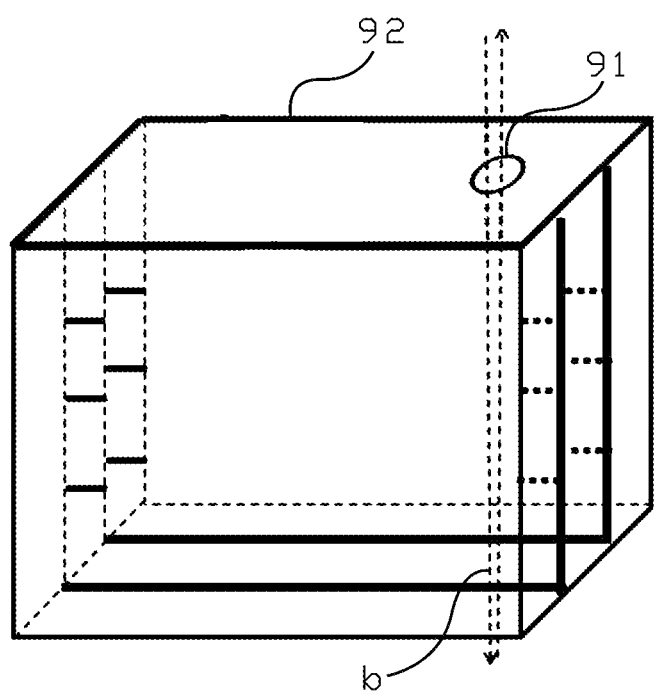
FIG. 5 is a schematic view showing the typical cartridge with a through hole on a top plate.

Referring to FIGS. 3 and 4, when the liquid crystal glasses 2 are displaced in the cartridge 1, the detecting process is described as below.

The electron-optical sensing device 31 arranged in the external side of the bottom of the cartridge 1 sends the optical signals from the bottom of the cartridge 1 toward the top plate 12. As the liquid crystal glasses 2 are displaced in the cartridge 1, the liquid crystal glass 2 blocks the optical signals and the reflective plate 32 are not able to receive the optical signals. In this way, the detecting device determines the cartridge 1 is not empty.

In other embodiments, the reflector may be other components capable of reflecting the sensing signals. For example, the top plate 12 may be made by directly coating a reflective layer on the internal surface of the top plate 12. In addition, the top plate 12 may be made by other reflective materials. In addition, the location of the reflective plate may be adjusted in accordance with the location of the electro-optical sensing device 31.

In view of the above, the detecting device includes an electro-optical sensing device for sending the optical signals to the internal of the cartridge and a reflector for receiving the optical signals from the electro-optical sensing device. The reflector is installed on the internal surface of the cartridge. The optical signals are used to detect whether the liquid crystal glass is displaced in the cartridge without passing through the top plate. In this way, as no through hole is needed on the top plate, the particles are prevented from getting into the cartridge.

It is believed that the present embodiments and their advantages will be understood from the foregoing description, and it will be apparent that various changes may be made thereto without departing from the spirit and scope of the invention or sacrificing all of its material advantages, the examples hereinbefore described merely being preferred or exemplary embodiments of the invention.

What is claimed is:

1. A detecting apparatus for determining whether liquid crystal glasses are displaced in a cartridge, comprising:
an electro-optical sensing device for sending sensing signals to an internal of the cartridge and for receiving the reflected signals from the internal of the cartridge;
a reflective plate installed in the internal of the cartridge for receiving the sensing signals from the electro-optical sensing device and for reflecting the sensing signals back to the electro-optical sensing device; and
wherein a determination of whether the liquid crystal glass is displaced in the cartridge is made by determining whether the reflected signals from the reflective plate are received after the sensing signals are sent.

2. The detecting component as claimed in claim 1, wherein the cartridge comprises a top plate, and the reflective plate is installed on an internal surface of the top plate.

3. The detecting component as claimed in claim 2, wherein the electro-optical sensing device is installed in an external side of a bottom of the cartridge.

4. The detecting component as claimed in claim 3, wherein the sensing signals are sent from the bottom of the cartridge toward the top plate.

5. The detecting component as claimed in claim 4, wherein the reflective plate is installed on an internal surface of the top plate capable of receiving the sensing signals.

6. A detecting apparatus for determining whether liquid crystal glasses are displaced in a cartridge, comprising:
an electro-optical sensing device for sending optical signals to an internal of the cartridge and for receiving the reflected signals from the internal of the cartridge;

a reflective plate installed in the internal of the cartridge for receiving the optical signals from the electro-optical sensing device and for reflecting the optical signals back to the electro-optical sensing device; and wherein a determination of whether the liquid crystal glass is displaced in the cartridge is made by determining whether the reflected signals from the reflective plate are received after the optical signals are sent.

7. The detecting component as claimed in claim 6, wherein the cartridge comprises a top plate, and the reflective plate is installed on an internal surface of the top plate.

8. The detecting component as claimed in claim 7, wherein the electro-optical sensing device is installed in an external side of a bottom of the cartridge.

9. The detecting component as claimed in claim 8, wherein the optical signals are sent from the bottom of the cartridge toward the top plate.

10. The detecting component as claimed in claim 9, wherein the reflective plate is installed on an internal surface of the top plate capable of receiving the optical signals.

11. A detecting apparatus for determining whether liquid crystal glasses are displaced in a cartridge, comprising:

a signal sensing device for sending sensing signals to an internal of the cartridge and for receiving the reflected signals from the internal of the cartridge;

a reflector installed in the internal of the cartridge for receiving the sensing signals from the signal sensing device and for reflecting the sensing signals back to the signal sensing device; and wherein a determination of whether the liquid crystal glass is displaced in the cartridge is made by determining whether the reflected signals from the reflector are received after the sensing signals are sent.

12. The detecting component as claimed in claim 11, wherein the cartridge comprises a top plate, and the reflector is installed on an internal surface of the top plate.

13. The detecting component as claimed in claim 12, wherein the signal sensing device is installed in an external side of a bottom of the cartridge.

14. The detecting component as claimed in claim 13, wherein the sensing signals are sent from the bottom of the cartridge toward the top plate.

15. The detecting component as claimed in claim 14, wherein the reflector is installed on an internal surface of the top plate capable of receiving the sensing signals.

16. The detecting component as claimed in claim 15, wherein the reflector is a reflective plate.

17. The detecting component as claimed in claim 15, wherein the signal sensing device is an electro-optical sensing device.

18. The detecting component as claimed in claim 15, wherein the sensing signals are optical signals.

* * * * *